United States Patent [19]
Matsuzawa

[11] Patent Number: 5,034,614
[45] Date of Patent: Jul. 23, 1991

[54] METHOD OF IMPROVING FLUORESCENCE YIELD

[75] Inventor: Sadao Matsuzawa, Tsukuba, Japan

[73] Assignee: Director-General of Agency of Industrial Science and Technology, Japan

[21] Appl. No.: 484,896

[22] Filed: Feb. 26, 1990

[30] Foreign Application Priority Data

Jun. 6, 1989 [JP] Japan .................................. 1-143898

[51] Int. Cl.$^5$ ............................................. G01N 21/64
[52] U.S. Cl. .............................. 250/459.1; 250/462.1; 250/461.1
[58] Field of Search ................ 250/459.1, 462.1, 461.1

[56] References Cited

U.S. PATENT DOCUMENTS 4,637,985  1/1987  Sidki et al. ........................... 436/518
4,851,195  7/1989  Matthews et al. ................ 250/459.1

Primary Examiner—Constantine Hannaher
Assistant Examiner—James E. Beyer
Attorney, Agent, or Firm—Lorusso & Loud

[57] ABSTRACT

The fluorescence yield of a solution containing a fluorescent substance is improved by treating the solution with carbon dioxide which may be in the form of a gas or a solid.

7 Claims, No Drawings

METHOD OF IMPROVING FLUORESCENCE YIELD

BACKGROUND OF THE INVENTION

This invention relates generally to a method of improving fluorescence yield and, more specifically, to a method of causing a fluorescent substance-containing solution to fluoresce with an improved fluorescence yield.

It is well known that certain compounds having one or more double bonds such as aromatic hydrocarbons, dyes and vitamins can produce fluorescence by irradiation of light. Also, certain compounds such as amino acids, sugars and metal compounds which do not fluoresce by themselves upon irradiation of light can also produce fluorescence when reacted with a fluorescence indicator. The term "fluorescence" used herein is intended to refer to emission of radiation from a substance as a result of excitation from a light source.

Fluorescence has been utilized in various fields such as for quantitative or qualitative analysis or measurement of chemical substances, laser oscillation, photochemical sensitization, and analysis of fluorescence characteristics (e.g. measurement of fluorescence life and flush photolysis). One problem associated with fluorescence is quenching, i.e. reduction of intensity of emission or reduction of quantum yield. The quenching causes reduction of sensitivity of fluorescence analysis, reduction of fluorescence life, reduction of efficiency of energy transfer from a fluorescent substance (sensitizer) to a reaction substrate in photochemical sensitization and reduction of efficiency for obtaining outlet in laser oscillation. Such quenching has been considered to be attributed to the presence of trace oxygen in the fluorescent substance-containing solution. Thus, to cope with this quenching problem, fluorescent substance-containing solution has been subjected to an oxygen-removing treatment by purging with nitrogen or argon gas, by warming with ultrasonic wave irradiation under reduced atmosphere or by repeated freezing, evacuation and melting operations. Such methods, however, incur relatively high treatment costs and long treatment time and, thus, are not fully satisfactory.

SUMMARY OF THE INVENTION

It is, therefore, an object of the present invention to provide a simple method which can effectively eliminate quenching and improve fluorescence yield.

In accomplishing the foregoing object, the present invention provides an improved method of causing a solution containing a fluorescent substance to produce fluorescence by irradiation of a light. The improvement involves a pretreatment step wherein the solution is treated with carbon dioxide before the irradiation to improve fluorescence yield thereof.

The treatment of the solution with $CO_2$ may be performed by contacting the solution with dry ice or by bubbling a $CO_2$-containing, oxygene-free gas through the solution.

Other objects, features and advantages of the present invention will become apparent from the detailed description of the invention to follow.

DETAILED DESCRIPTION OF THE INVENTION

In the present invention, a fluorescent substance-containing solution is contacted with $CO_2$ so that $C_2$ is dissolved in or absorbed by the solution. By this simple treatment, the fluorescence yield of the solution is surprisingly improved. Mechanisms of such a quenching-prevention effect has not been clarified yet. Since the contact with $CO_2$ gas gives better results than those obtained by the contact with $N_2$ gas, the $CO_2$ absorbed in the solution is considered to play a role in preventing quenching.

The present invention may be utilized for improving fluorescence yield of any fluorescent substance which, in solution, produces fluorescence upon irradiation of a light. Examples of the fluorescent substances include:

(1) fluorescent compounds such as aromatic hydrocarbons (e.g. naphthalene, biphenyl, fluorene, acenaphthene, anthracene, phenanthrene, chrysene, coronene, fluoranthene, pyrene, perylene, o-terphenyl, p-terphenyl, triphenylene, 9-cyanoanthracene, 9,10-dicyanoanthracene), azine dyes (e.g. lumiflavin, riboflavin, FAD, FMN), coumarin dyes (e.g. coumarylpyrone), xanthene dyes (e.g. fluorescein, FlBr, FlI, rhodamine B, rhodamine 6G), cyanine dyes, stilbene derivatives, oxazole, and oxadiazole derivatives;

(2) intermediate compounds such as exciplexes of an aromatic hydrocarbon with an aromatic amine (e.g. dimethylaniline or diethylaniline), exciplexes of an aromatic hydrocarbon with a pyrrole compound (e.g. trimethylpyrrole), and exciplexes of an aromatic hydrocarbon with a cyanide compound (e.g. dicyanobenzene or dicyanoanthracene); and (3) reaction products such as between an inorganic compound and a fluorescence derivatizing reagent (e.g. 8-quinolinol or its derivative, salicylidene-o-aminophenol or the like Shiff base, an azo compound, a flavonoid, a diamino compound, a cation dye, an anion dye, nitronaphthylamine, salicylic acid, a benzotiazole compound or an anthraquinone derivative) and between an organic compound (e.g. a vitamine, a penicillin, a morphine, a sulfanylamide, histamine, an amino acid, a carboxylic acid or a sugar) and a fluorescence derivatizing reagent.

Any solvent can be used for dissolving the above fluorescent substance. Both polar solvents such as water and alcohols and non-polar solvents such as hydrocarbons may be used. A mixed solvent system may be suitably used. In the case of photochemical sensitization, for example, water, methanol, ethanol, diethyl ether, toluene, cyclohexane or a mixture thereof is generally used.

According to the present invention the fluorescent substance-containing solution is pretreated with $CO_2$ so that $CO_2$ is dissolved in or absorbed by the solution. The pretreatment can be suitably carried out by charging the solution into a vessel such as a flask, a cell or a test tube and, then, bubbling a $CO_2$-containing gas through the solution within the vessel. Alternatively, the pretreatment may be effected by contacting the solution with dry ice in a vessel.

In either case, it is preferred that the vessel have such a structure as to prevent air from entering therein during the treatment of the solution with the $CO_2$. Further, the use of fine bubbles or finely divided dry ice is preferred for reasons of improving efficiency of the contact and of minimizing entrapment of air.

The pretreatment with dry ice is particularly preferable for reasons of simplicity and effectiveness of the treatment. The amount of dry ice is generally 0.2–1.5 g, preferably 0.3–1 g per 10 ml of the solution to be treated. The amount of dry ice, however, varies with the kind and amount of the solvent of the solution and may be outside of the above range.

Commercially available dry ice or $CO_2$ gas may be used as such for the purpose of the present invention. If desired, specifically purified dry ice or $CO_2$ gas may be used.

The fluorescent substance-containing solution thus treated is then subjected to irradiation of an external light source for the purpose of effecting, for example, dye laser or photochemical sensitization. The fluorescent substance-containing solution treated with $CO_2$ in accordance with the present invention exhibits improved fluorescence yield and fluorescence life. Further, the fluorescence yield remains substantially unchanged even after the treated solution has been allowed to stand in ambient air for several hours. In this respect, too, the present invention is advantageous over a known purging method using nitrogen or argon gas.

The following examples will further illustrate the present invention.

EXAMPLE 1

Naphthalene was dissolved in n-hexane to obtain a solution having a naphthalene concentration of $1 \times 10^{-4}$ M (mole/liter). Dry ice particles were then added to the solution in an amount of 0.15 g per 3 ml of the solution. A fluorescence analysis revealed that the fluorescence intensity of the $CO_2$-treated solution was about 17.5 times as high as that of the non-treated solution.

EXAMPLE 2

Anthracene was dissolved in ethanol to obtain a $5 \times 10^{-4}$ M solution. Dry ice particles were then added to the solution in an amount of 0.15 g per 3 ml of the solution. A fluorescence analysis revealed that the fluorescence intensity of the $CO_2$ treated solution was about 1.3 times as high as that of the nontreated solution.

EXAMPLE 3

Rhodamine B was dissolved in ethanol to obtain a $5 \times 10^{-4}$ M solution. Dry ice particles were then added to the solution in an amount of 0.15 g per 3 ml of the solution. A fluorescence analysis revealed that the fluorescence intensity of the $CO_2$-treated solution was about 1.1 times as high as that of the non-treated solution.

COMPARATIVE EXAMPLE 1

Example 1 was repeated in the same manner as described except that the pretreatment of the naphthalene solution with dry ice was not performed but, instead, $N_2$ gas was bubbled through the solution at a rate of 20 ml/minute for 30 minutes. The fluorescence intensity of the $N_2$-treated solution was about 14.5 times as high as that of the non-treated solution.

COMPARATIVE EXAMPLE 2

Example 2 was repeated in the same manner as described except that the pretreatment of the anthracene solution with dry ice was not performed but, instead, $N_2$ gas was bubbled through the solution at a rate of 20 ml/minute for 30 minutes. The fluorescence intensity of the $N_2$-treated solution was about 1.2 times as high as that of the non-treated solution.

COMPARATIVE EXAMPLE 3

Example 3 was repeated in the same manner as described except that the pretreatment of the rhodamine B solution with dry ice was not performed but, instead, $N_2$ gas was bubbled through the solution at a rate of 20 ml/minute for 30 minutes. The fluorescence intensity of the $N_2$-treated solution was about 1.06 times as high as that of the non-treated solution.

EXAMPLE 4

Benzene, naphthalene, anthracene, phenanthrene and pyrene were each dissolved in n-hexane to give solutions with concentrations in the range of between $1 \times 10^{-6}$ and $1 \times 10^{-3}$ M. Dry ice particles were then added to each solution in an amount of 0.15–0.2 g per 3 ml of the solution. The fluorescence life was then measured to give the results summarized in Table 1 below.

COMPARATIVE EXAMPLE 4

Example 4 was repeated in the same manner as described except that the pretreatment with dry ice was substituted by that of $N_2$ bubbling. The results are shown in Table 1.

TABLE 1

| Fluorescent Substance | Fluorescence Life ($\times 10^{-9}$ sec.) | |
|---|---|---|
| | Treated with dry ice | Treated with $N_2$ |
| Benzene | 28.4 | 15.8 |
| Naphthalene | 97.9 | 82.8 |
| Anthracene | 5.57 | 4.65 |
| Phenanthrene | 54.3 | 39.9 |
| Pyrene | 464 | 360 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method for producing a fluorescence from a solution consisting essentially of a non-aqueous solvent and a fluorescent substance dissolved in said solvent, said method comprising:
   placing said solution in a closed container;
   contacting said solution in said container with carbon dioxide to dissolve or absorb carbon dioxide into said solution, while preventing air from entering the container; and then
   exposing said solution to a light source to excite said fluorescent substance and thereby produce fluorescence.

2. A method as claimed in claim 1, wherein said contacting is performed by contacting said solution with dry ice.

3. A method as claimed in claim 2, wherein said contacting is performed by adding dry ice particles to said solution.

4. A method as claimed in claim 1, wherein said contacting is performed by bubbling a carbon dioxide gas through said solution.

5. A method for producing fluorescence in accordance with claim 1 wherein said dissolved or absorbed carbon dioxide serves to prevent oxygen quenching.

6. A method in accordance with claim 1 wherein said nonaqueous solvent is selected from the group consisting of alcohols and non-polar hydrocarbon solvents.

7. A method in accordance with claim 1 wherein said nonaqueous solvent is selected from the group consisting of methanol, ethanol, diethylether, toluene, cyclohexane and mixtures thereof.

* * * * *